United States Patent
Murty et al.

(10) Patent No.: US 6,503,532 B1
(45) Date of Patent: Jan. 7, 2003

(54) PHARMACEUTICAL COMPOSITION CONTAINING TETRAHYDROCANNABINOL AND A TRANSDERMAL/TRANSCUTANEOUS DELIVERY METHOD THEREOF

(75) Inventors: Ram B. Murty, Lexington, KY (US); Dipak K. Chowdhury, Lexington, KY (US); Murty Mangena, Lexington, KY (US)

(73) Assignee: Murty Pharmaceuticals, Inc., Lexington, KY (US)

( * ) Notice: Subject to any disclaimer, the term of this patent is extended or adjusted under 35 U.S.C. 154(b) by 0 days.

(21) Appl. No.: 10/121,579

(22) Filed: Apr. 15, 2002

Related U.S. Application Data

(60) Provisional application No. 60/283,350, filed on Apr. 13, 2001.

(51) Int. Cl.[7] .......................... A61F 13/00; A61K 9/70; A61L 15/16
(52) U.S. Cl. ................. 424/449; 424/443; 424/447
(58) Field of Search ................. 424/443, 447, 424/449

(56) References Cited

U.S. PATENT DOCUMENTS 6,248,363 B1 * 6/2001 Patel et al. .............. 424/497

* cited by examiner

Primary Examiner—Thurman K. Page
Assistant Examiner—Humera N. Sheikh
(74) Attorney, Agent, or Firm—Townsend & Banta

(57) ABSTRACT

A transdermal/transcutaneous delivery system to deliver Tetrahydrocannabinol (THC) and related compounds, comprising of gel, film and reconstituted liquid for topical application. The delivery system may contain polymethacrylic acid (PMA), carbopol, polyethylene glycol 8000 (PEG), propylene glycol (PG), water, alcohol, acetone, caprylic acid, caproic acid, oleic acid, lauric acid, isopropyl myristate, triethanolamine, and mixtures thereof. This formulation can be used as an analgesic, antiemetic, antiglaucoma medication, arthritis treatment and prevention of weight loss treatment associated with AIDS. It can also be used for treating dementia and multiple sclerosis. The present formulation avoids the problems associated with oral administration, patient compliance and potential abuse associated with other routes of administration of THC.

27 Claims, 4 Drawing Sheets

PHARMACEUTICAL COMPOSITION CONTAINING TETRAHYDROCANNABINOL AND A TRANSDERMAL/TRANSCUTANEOUS DELIVERY METHOD THEREOF

This application claims the benefit of Provisional application Ser. No. 60/283,350, filed Apr. 13, 2001.

FIELD OF THE INVENTION

The present invention provides a pharmaceutical composition containing Tetrahydro Cannabinol (THC), having analgesic, anti-emetic, anti-nausea and anti-glaucoma properties, which is easily absorbed into the body at a steady rate to achieve a desired concentration in the bloodstream. Further, methods are provided for forming the pharmaceutical composition into a gel or powder, and for applying the gel or powder to form of the pharmaceutical composition to a transdermal patch for application to a human or animal body.

BACKGROUND OF THE INVENTION

Marijuana contains many compounds. The major active compound thereof has been identified as DELTA.Sup Tetrahydrocannabinol (THC), also known as DELTA 9-THC depending on the carbon numbering convention used. THC and other compounds in marijuana have, in addition to promoting psychoactivity, been reported to provide beneficial effects. There are many research publications reporting beneficial activities like analgesic, antiemetic, and antiglaucoma effects. It has also been found that a major contributor of these beneficial effects is THC.

THC is effective as an analgesic, antiemetic, in anorexia, and for treating the nausea and frequent vomiting caused by cancer chemotherapy. THC is currently being given only orally, but is occasionally ineffective when taken in this form. For example, a metaanalysis study revealed a poor or only partial response to THC in approximately 65% of 750 courses of oral therapy. Thus, high single doses are administered which may cause undesirable side effects such as sedation, confusion and anxiety. Such poor response to oral administration of THC may be due to the limited aqueous solubility of THC, its extensive first pass metabolism following oral administration, and the resulting low absolute bioavailability of THC (13% on an average).

In addition, it has been noted that fasting or food deprivation could decrease the rate of absorption of THC from sesame oil capsules currently available in the market. Previous studies have also reported that another limitation of orally administered THC is the large intersubject variability in absorption. For this reason it would be important to titrate the THC dose on an individual basis, since the drug has biphasic activity and a relatively narrow therapeutic index.

In an attempt to overcome such problems, transdermal patches have been proposed. For example, U.S. Pat. No. 6,113,940 discloses a "patch-like" device, utilizing a backing layer with a reservoir for holding the cannabis. The cannabis preparation uses, as a carrier for the cannabis preparation, a polymer matrix (the cannabis being suspended within the polymer matrix.). This method uses a "porous membrane, nonporous membrane, polymer film, polymer membrane."

As with the above delivery system, U.S. Pat. No. 6,132,762 consists of a "patch-like" device containing a reservoir for holding a cannabis preparation. The reservoir therein holds a gel comprised of at least one member selected from the group consisting of guar gum, gelatin, carboxymethylcellulose, carrageenan and agar. Additional steps of heating and cooling the formulation are needed prior to its intended use of treating joint pain, muscle pain or arthritis. Further, the backing layer contemplates an adhesive for holding the backing layer on/against the skin of the user.

U.S. Pat. No. 6,328,992 addresses the problems discussed above by providing a cannabis preparation comprising a 1–50 weight percent cannabis, 1–15 weight percent skin enhancer and about 10–90 weight percent of a transdermal carrier that may, as with a number of the previously discussed patents, be placed on a patch, strip, bandage and covering for holding the preparation. The transdermal carrier may be comprised of natural rubber, viscoelastic semi-solid materials, hydrogels, thermoplastic polymers, elastomer, amnd thermoelastomers, as well as an oil selected mineral oils, vegetable oils, fish oils, animal oils, carbon tetrachloride, ethanolic solutions of resins and pyrahexyl mixtures. To achieve its desired purpose, the preparation, an aggregation of numerous cannabinols, is delivered at a rate of 17 ug/sq.cm./hour.

However, all of the above encounter various problems. In view of the problems encountered with oral administration of THC as discussed above, the present inventors performed extensive research in order to provide a safe, reliable and effective method of delivery of THC, and a composition to use in performing same. It was then unexpectedly discovered by the present inventors that the problems associated with oral administration of THC can be minimized by the administration of the pharmaceutical composition containing THC of the present invention, which provides sustained low doses of THC via a transdermal route. Further, it was found that forming the composition of the present invention into a gel formulation as disclosed herein, which is applied on the skin of the patient's body, or by applying as a transdermal patch on the skin of the patient's body, provides a very effective method of delivery of the active ingredient.

Specifically, a pharmaceutical composition is provided consisting of between 1–10% by weight of THC (including specifically delta-9 THC, and more generally, all cannabinols), 1–5% of enhancer, 0.5%–5% neutralizer and a carrier containing approximately 70% alcohol and 25% water, rather than the enumerated oils and elastomer materials disclosed in U.S. Pat. No. 6,328,992. Further, there is no need in the present invention to use polyisoprene elastomers and styrene-butadiene block co-polymers in the formulation. Rather, the present invention uses polymers of acrylic acid and polymers of acrylic acid crosslinked with allylpetnearythritol. This composition of the present invention is able to overcome the difficulties discussed above, and achieve the objects of the present invention, by providing a pharmaceutical composition containing a relatively low dose of delta-9 THC (but with the potential to use other cannibinols) with a delivery rate of only 10.8 ug/sq.cm./hour (to treat nausea and loss of appetite).

SUMMARY OF THE INVENTION

In view of the deficiencies associated with the oral methods of delivery of THC discussed above, as well as conventional transdermal patches, it is an object of the present invention to provide a pharmaceutical composition containing tetrahydrocannabinol, which can be applied via a transdermal/transcutaneous route to a patient.

In view of the above, in a first embodiment of the present invention, a pharmaceutical composition is provided comprising tetrahydrocannabinol (THC), ethanol, polyethylene glycol, polymethacrylic acid, isopropyl myristate, carbopol, triethanolamine, propylene glycol, and acetone.

In a second embodiment of the present invention according to the first embodiment above, a pharmaceutical composition is provided, comprising:

from greater than 0 to 5 wt % tetrahydrocannabinol (THC);
40–70 wt % ethanol;
3–10 wt % polyethylene glycol;
5–20 wt % polymethacrylic acid;
from greater than 0 to 5 wt % isopropyl myristate;
from greater than 0 to 10 wt % carbopol;
from greater than 0 to 5 wt % triethanolamine;
5–50 wt % propylene glycol; and
20–50 wt % acetone.

In a third embodiment of the present invention according to the first embodiment above, a pharmaceutical composition is provided, comprising:

about 0.5 to about 2 wt % tetrahydrocannabinol (THC);
about 65 wt % ethanol;
about 4.7 to about 5.7 wt % polyethylene glycol;
about 10 to about 14 wt % polymethacrylic acid;
about 0.5 to about 1 wt % isopropyl myristate;
from greater than 0 to about 5 wt % carbopol;
from about 0.47 to about 1 wt % triethanolamine;
from about 10 to about 30 wt % propylene glycol;
about 35 wt % acetone, and
water.

In a fourth embodiment of the present invention, a pharmaceutical composition is provided according to the first embodiment described above, further containing a permeation enhancer.

In a fifth embodiment of the present invention, a pharmaceutical composition is provided according to the fourth embodiment above, wherein the pharmaceutical composition contains 2–10 wt % permeation enhancer.

In a sixth embodiment of the present invention, a pharmaceutical composition is provided according to the fourth embodiment above, wherein the pharmaceutical composition contains about 5 wt % permeation enhancer.

In a seventh embodiment of the present invention, a pharmaceutical composition is provided according to the fourth embodiment above, wherein the permeation enhancer is caproic acid.

In an eighth embodiment of the present invention, a pharmaceutical composition is provided according to the fourth embodiment above, wherein the permeation enhancer is caprylic acid.

In a ninth embodiment of the present invention, a pharmaceutical composition is provided according to the fourth embodiment above, wherein the permeation enhancer is lauric acid.

In a tenth embodiment of the present invention, a pharmaceutical composition is provided according to the fourth embodiment above, wherein the permeation enhancer is oleic acid.

In an eleventh embodiment of the present invention, a pharmaceutical composition is provided according to the fourth embodiment above, wherein the permeation enhancer is TWEEN 80.

In a twelfth embodiment of the present invention, a pharmaceutical composition is provided according to the fourth embodiment above, wherein the permeation enhancer is selected from the group consisting of caproic acid, caprylic acid, lauric acid, oleic acid and TWEEN 80.

In a thirteenth embodiment of the present invention, a method of manufacturing the composition of the first through tenth embodiments described above is provided, the method comprising:

(a) combining/mixing ethanol, polyethylene glycol, polymethacrylic acid, tetrahydrocannabinol (THC), isopropyl myristate, carbopol, triethanolamine, optionally a permeation enhancer, propylene glycol, acetone, and water to form a complex;
(b) drying the complex using heat to form a dried complex;
(c) milling the dried complex to form a powder; and
(d) adding a lower alcohol to the powder to form a gel.

In a fourteenth embodiment of the present invention according to the thirteenth embodiment above, a method of manufacturing the composition of the first through eighth embodiments described above is provided, the method further comprising:

mixing the elements in step (a) at a temperature of from 25–70° C.

In a fifteenth embodiment according to the thirteenth embodiment above, a method of manufacturing the composition of the first through twelfth embodiments described above is provided, the method further comprising:

drying the complex is step (b) at a temperature of from 25–70° C.

In an sixteenth embodiment according to the thirteenth embodiment above, a method of manufacturing the composition of the first through twelfth embodiments described above is provided, the method further comprising:

performing the drying step (b) for 4–12 hours.

In an seventeenth embodiment according to the thirteenth embodiment above, a method of manufacturing the composition of the first through twelfth embodiments described above is provided, the method further comprising:

mixing the components in step (a) for 1–4 hours.

In an eighteenth embodiment according to the thirteenth embodiment above, a method of manufacturing the composition of the first through twelfth embodiments described above is provided, the method further comprising:

mixing the components in step (a) at a stirring rate of 60–300 RPM's.

In a nineteenth embodiment of the present invention, a method of manufacturing the composition of the first through twelfth embodiments described above is provided, the method further comprising:

(a) combining/mixing ethanol, polyethylene glycol, polymethacrylic acid, tetrahydrocannabinol (THC), isopropyl myristate, carbopol, triethanolamine, a permeation enhancer, propylene glycol, acetone, and water at a temperature of from 25–70° C., and stirring same at a rate of 60–300 RPM's for 1–4 hours to form a complex;
(b) drying the complex at a temperature of from 25–70° C. for 1–4 hours to form a dried complex;
(c) milling the dried complex to form a powder; and
(d) adding a lower alcohol to the powder to form a gel.

In a nineteenth embodiment of the present invention, a method of manufacturing the composition of the first through twelfth embodiments described above is provided, the method further comprising:

(a) combining/mixing ethanol, polyethylene glycol, polymethacrylic acid, tetrahydrocannabinol (THC), isopropyl myristate, carbopol, triethanolamine, a permeation enhancer, propylene glycol, acetone, and water at a temperature of from 40–60° C., and stirring same at a rate of 60–300 RPM's for 1–4 hours to form a complex;

(b) drying the complex at a temperature of from 40–60° C. for 1–4 hours to form a dried complex;
(c) milling the dried complex to form a powder; and
(d) adding a lower alcohol to the powder to form a gel.

In a twentieth embodiment of the present invention, a method of manufacturing the pharmaceutical composition of the first through twelfth embodiment described above is provided comprising:

mixing carbopol and polymethacrylic acid in ethanol to form a first solution;

mixing polyethylene glycol or polypropylene glycol in ethanol to form a second solution;

mixing the first and second solutions to form a third solution;

mixing isopropyl myristate and triethanolamine into the third solution as necessary;

mixing tetrahydrocannabinol with ethanol to form a fourth solution;

mixing the third and fourth solutions to form a pharmaceutical composition according to the present invention.

In an twenty first embodiment of the present invention, a transdermal/transcutaneous delivery system for THC is provided comprising the pharmaceutical composition of the first through twelfth embodiments described above.

A twenty second embodiment of the present invention is provided according to the twenty first embodiment described above, wherein the transdermal/transcutaneous delivery system further comprises a gel, patch or cloth for application onto the skin of a patient.

In twenty third embodiment of the present invention, a method for manufacturing the gel, patch or cloth of the twenty second embodiment described above is provided comprising addition of the gel formed in the second embodiment to a patch or cloth suitable for application in human or animal skin.

In a twenty fourth embodiment of the present invention, a method of manufacturing a transdermal patch or cloth containing a pharmaceutical composition containing THC is provided comprising addition of carbopol/poly methacrylic acid in Ethanol to Poly ethylene glycol or Propylene glycol in ethanol to form a first solution, mixing the first solution with a solution containing isopropyl myristate or triethanolamine to form a second solution, mixing the second solution with a mixture of tetrahydrocannabinol and ethanol to obtain a viscous solution or gel, and applying the viscous solution or gel to a transdermal patch or cloth for direct application to human or animal skin.

In the twenty-fifth embodiment of the present invention, a method of manufacturing gel containing a pharmaceutical composition containing tetrahydrocannibinol ($\Delta 9$ THC) is provided comprising a first step of mixing carbopol and trolamine in an ethanol:water mixture to form a first viscous solution, a second step of mixing the first viscous solution with a second solution containing ethanol and isopropyl myristate to obtain a third solution, and a third step comprising mixing the third solution with a fourth solution containing $\Delta 9$ THC and ethanol to obtain a gel for the direct application to human and/or animal skin.

In the twenty-sixth embodiment of the present invention, a method for manufacturing a pharmaceutical composition comprising a transdermal gel containing extracts of cannabis is provided comprising a first supercritical fluid extraction step wherein 9 THC is extracted from cannabis, a second step comprising dispersing the 9 THC in an ethanol:water mixture, a third step comprising adding trolamine to the ethanol:water mixture to form a first solution, a fourth step comprising mixing the first solution with a second solution containing ethanol and isopropyl myristate to form a third solution, wherein the third solution is a translucent gel for direct application to human skin.

DETAILED DESCRIPTION OF THE INVENTION

Figure 1:
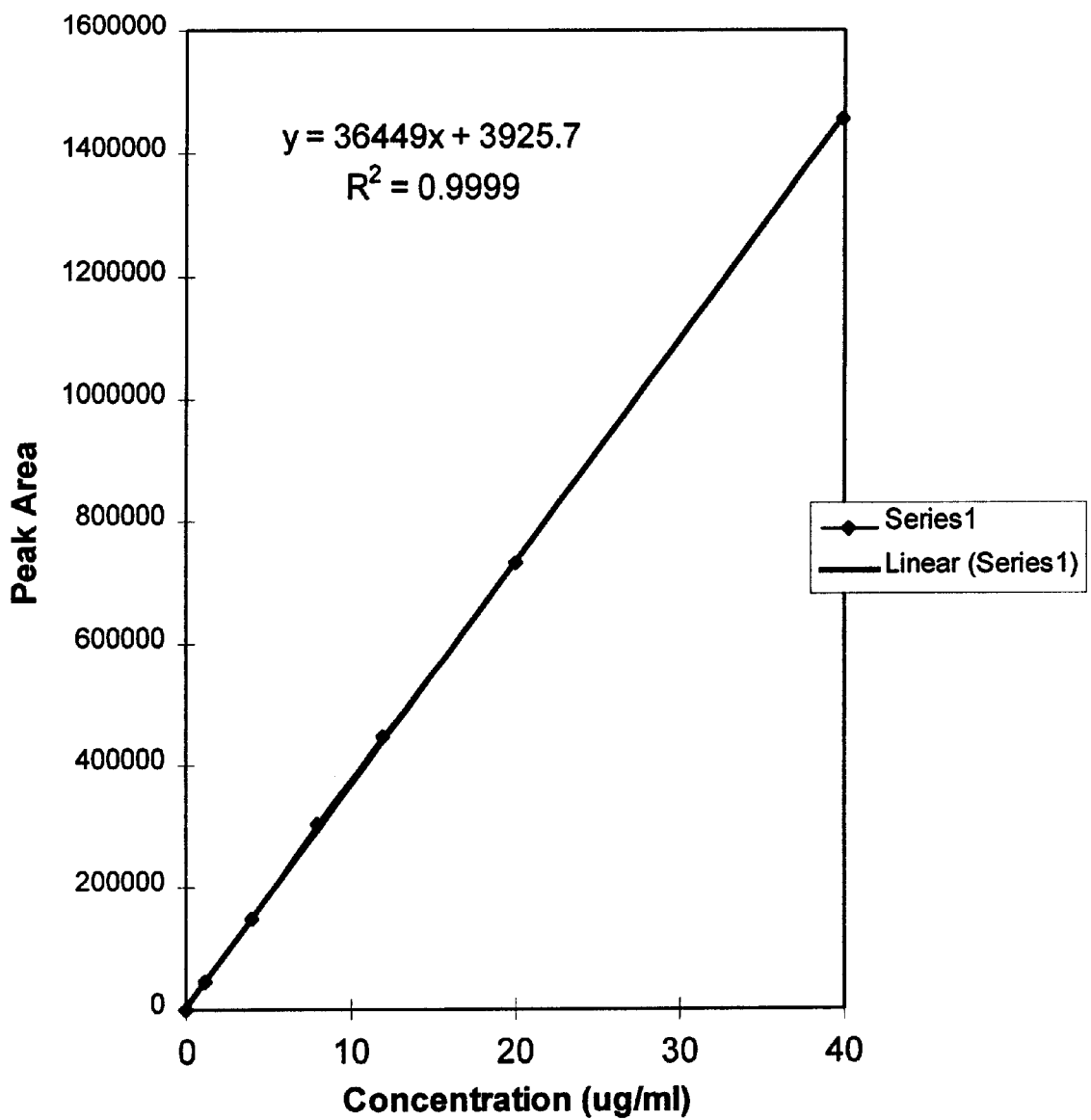
FIG. 1 is graph illustrating the standard curve for concentration of THC in a solution vs. the peak area.

Drug transportation rates through the skin are generally low, but therapeutic plasma levels can be achieved for drugs with suitable properties. That is, the drug should be highly potent, the daily dose requirement should be low, and therapeutic plasma levels should be ~10 nanograms/ml. Plasma levels for therapeutic effects of THC are in the range of 10 nanograms/ml, making THC a suitable candidate for transdermal administration.

The source of THC and related compounds used are usually crude extracts of marijuana plants, the purified form of the drug being obtained by supercritical fluid extraction (SCFE) of the crude extracts or other suitable extraction methods. However, synthetic forms may be utilized.

Solubility of the active ingredient THC in the carrier is a very important consideration when preparing the pharmaceutical composition of the present invention, and should be assessed before making any transdermal delivery. Thus, solubility of THC alone was determined by the present inventors in a 70:30 water:alcohol (v/v) mixture, a 50:50 water:alcohol (v/v) mixture, as well in 30:70 water:alcohol (v/v) mixtures containing various permeation enhancers. The solubility tests for each of the samples was performed as follows:

Approximately 50–60 mg of THC was placed into each of six different centrifuge tubes. In each of these centrifuge tubes, 1 ml of ethanol:water solution (70:30 v/v) and 5% v/v (volume solute per volume of solvent) of permeation enhancer (caproic acid, caprylic acid, TWEEN 80, lauric acid and oleic acid, for each of test samples 3–7, respectively) was added thereto. The centrifuge tubes were then mechanically agitated at room temperature for 24 hours. The samples were then centrifuged at 3500 rpm for 5 minutes and filtered through a $0.2\mu$ whatman filter. The filtrate was diluted and analyzed by HPLC. The solubility of THC in test samples 1–7 is given in Table I below.

TABLE I

| Test Sample Number | Amount of THC in diluted sample | Dilution factor | Amount of THC in the solubilized sample | Solvent System alcohol:water |
|---|---|---|---|---|
| 1. (THC alone) | 57.14 ug/ml | 50 | 2.86 mg/ml | 50:50 |
| 2. (THC alone) | 404.22 ug/ml | 50 | 20.21 mg/ml | 70:30 |

TABLE I-continued

| Test Sample Number | Amount of THC in diluted sample | Dilution factor | Amount of THC in the solubilized sample | Solvent System alcohol:water |
|---|---|---|---|---|
| 3. (THC & Caproic acid) | 344.65 ug/ml | 50 | 17.23 mg/ml | 70:30 |
| 4. (THC & Caprylic acid) | 809.48 ug/ml | 50 | 40.47 mg/ml | 70:30 |
| 5. (THC & TWEEN 80) | 363.42 ug/ml | 50 | 18.17 mg/ml | 70:30 |
| 6. (THC & Lauric acid) | 738.86 ug/ml | 50 | 36.94 mg/ml | 70:30 |
| 7. (THC & Oleic acid) | 244.44 ug/ml | 50 | 12.22 mg/ml | 70:30 |

As shown above, Test Sample #1 was dissolved in a 50:50 ethanol:water solution, but after centrifugation and filtration, the concentrated solution was hazy. After analyzation, solubility in such a solution without permeation enhancer and a high concentration of water was found to be very low (2.86 mg/ml). When the solvent system was changed to 70:30 (ethanol: water) solubility of THC was increased appreciably (20.21mg/ml). However, it was found that the solubility of THC could be dramatically increased (almost doubled) be including either of two permeation enhancers, caprylic acid or lauric acid, in the THC containing solution.

The pharmaceutical composition of the present invention may be formed into a gel or powder composition for transdermal/transcutaneous application. The methods of manufacturing such variations of the pharmaceutical composition are shown below. However, the methods of manufacturing said composition should not be limited solely to the examples below.

Formulation of Powder:

Polymethacrylic acid (PMA 100,000) and polyethylene glycol (PEG-8000) were dissolved in ethanol in two different beakers utilizing a stirring waterbath (40–45° C.). The ratio of polymethacrylic acid to polyethylene glycol (PMA:PEG) was 2:1. Both the solutions were mixed until they formed a clear solution. The solutions were then cooled to room temperature. Water was then added to each of the two solutions in increments of 1 g, and at the addition of 10 g, the solution formed a whitish gel. The gel was collected and dried in an oven. The dried mass (PMA-PEG complex) was then ground to powder. A powder complex was prepared with PEG-20000, but the agglomerate was so hard that it was difficult to grind to powder. Therefore, PEG-8000 was used for making the complex to get a free flowing powder.

A 10% solution was made by dissolving the PMA-PEG complex made above in a 65:35 acetone:ethanol mixture using continuous stirring. The resulting solution formed a viscous solution.

THC (tetrahydrocannabinol) solution was then prepared by dissolving THC in ethanol. This THC solution was then added to the PMA-PEG complex solution produce above, as well as with a permeation enhancer. Initially, two formulations (formulations 1 &2) were prepared (containing 25 mg/ml and 14.6 mg/ml of THC each, respectively) and analyzed to determine the percent recovery. Later six formulations (formulations 3 to 8) were prepared containing differing amounts of THC alone and in combination with permeation enhancers. Another PMA of low molecular weight 15000 was also used forming a complex with PEG-8000. Six more formulations (Formulations 9 to 14) were prepared using the complex powder and permeation enhancer. For these six formulations 9–14, the ratio of the solvent system of acetone:ethanol: water was 65:25:10, respectively.

A powder complex could not be prepared by using Polyacrylic acid (PAA 450,000) and PEG 8000 because a gel was instantly formed and, after drying, the gel formed a plastic-like mass which was difficult to grind.

All of the above formulations 1–14 were then analyzed by HPLC. The results of the HPLC analysis are shown below in Table II.

TABLE II

| Test Product | Permeation enhancer: | Polymers: | Amount of THC added: | Percent recovery |
|---|---|---|---|---|
| Formulation-1 | — | PMA100000-PEG 8000 complex | 14.16 mg/ml | 79.02 |
| Formulation-2 | — | PMA100000-PEG 8000 complex | 25.1 mg/ml | 71.39 |
| Formulation-3 | — | PMA100000-PEG 8000 complex | 10.16 mg/ml | 84.61 |
| Formulation-4 | Oleic acid | PMA100000-PEG 8000 complex | 10 mg/ml | 98.74 |
| Formulation-5 | Lauric acid | PMA100000-PEG 8000 complex | 10 mg/ml | 99.71 |
| Formulation-6 | Caproic acid | PMA100000-PEG 8000 complex | 11.96 mg/ml | 89.16 |
| Formulation-7 | Caprylic acid | PMA100000-PEG 8000 complex | 9.46 mg/ml | 91.15 |
| Formulation-8 | TWEEN 80 | PMA100000-PEG 8000 complex | 10.03 mg/ml | 93.03 |
| Formulation-9 | Lauric acid | PMA15000-PEG8000 complex | 10.46 mg/ml | 88.14 |
| Formulation-10 | Oleic acid | PMA15000-PEG8000 complex | 10.43 mg/ml | 84.75 |
| Formulation-11 | Caprylic acid | PMA15000-PEG8000 complex | 10.46 mg/ml | 88.81 |
| Formulation-12 | Caproic acid | PMA15000-PEG8000 complex | 10.36 mg/ml | 86.1 |
| Formulation-13 | Tween 80 | PMA15000-PEG8000 complex | 10.26 mg/ml | 86.5 |
| Formulation-14 | — | PMA15000-PEG8000 complex | 9.26 mg/ml | 82.2 |

The following gel and film formulations were prepared with PMA (100000) and PEG (8000).

Formulation of Gel:

1.26 g of polymethacrylic acid (PMA 100,000) was dissolved in a 75% v/v alcohol: 25% v/v water mixture using continuous stirring at 45–50C. After 2 hours of continuous stirring, a viscous solution was formed. Then, about 2.0 g of PEG-8000 was dissolved in alcohol with continuous stirring in a water bath at a temperature 45–50° C.). Both the PMA and PEG solutions were mixed until they formed a clear solution. The clear solution was kept at room temperature. The PMA: PEG ratio was 1.25:2.74 mg of THC was then dissolved in 1 ml of alcohol, and the resulting THC solution was then poured into the viscous PMA:PGA complex solution, and continuously stirred. A clear gel was formed (Formulation-16). Five more formulations (Formulations 17 to 21) were then prepared in the same method. However, a 5 wt % of permeation enhancer was added to each of formulations 17–21.

Five more formulations (Formulation 28 to 32) were prepared using a solution having a PMA:PEG ratio of 2:1. All these formulations were then subjected to HPLC analysis to determine the percent recovery and physical appearance of the gel formulation, the results of these HPLC tests being shown in Table III below:

TABLE III

| Test product | Permeation enhancer: | Amount of THC added: | Physical appearance of gel: | Percent recovery: |
|---|---|---|---|---|
| Formulation-16 | — | 74.0 mg | Transparent and light yellow in color | 88.6 |
| Formulation-17 | Lauric acid | 99.8 mg | Transparent and reddish yellow in color | 103.56 |
| Formulation-18 | Tween 80 | 97.8 mg | Translucent, very light yellow and TWEEN 80 separated | |
| Formulation-19 | Oleic acid | 75.5 mg | Translucent and very light yellow in color | 63.22 |
| Formulation-20 | Caprylic acid | 70.00 mg | Transparent and reddish yellow in color | 89.61 |
| Formulation-21 | Caproic acid | 76.5 mg | Transparent and reddish yellow | 92.98 |
| Formulation-28 | Oleic acid | 80.5 mg | Translucent and gray colored | 81.29 |
| Formulation-29 | Lauric acid | 83.0 mg | Translucent and light yellow in color | 89.41 |
| Formulation-30 | Caprylic acid | 85.5 mg | Transparent and light yellow in color | 82.27 |
| Formulation-31 | Caproic acid | 89.3 mg | Transparent and light yellow in color | 84.47 |
| Formulation-32 | — | 78.6 mg | Transparent and light yellow in color | 84.30 |

Gel formulations were prepared with Polymethacrylic acid (PMA 15000) and Polyacrylic acid (60000). Both of these compounds are commercially available as a sodium salt solution. However, formulations containing these compounds failed to form a gel after mixing with PEG-8000 solution. Polyacrylic acid (450,000) formed a gel with PEG-8000. But, it was an opaque gel, and not used since all the gel formulations should preferably be transparent.

Initially, two placebo gel formulations #1 and #2, for use in vivo testing, were prepared using two different concentrations of Carbopol as follows:

Placebo Gel Formulation #1

Carbomer 934 (lot# 00-218) 0.1 g

Deionized water 5.41 g

Isopropyl myristate (Lot#00-219) 0.148 g

Alcohol (200 Proof) 14.2 g

Trolamine (triethanolamine) (lot# 00-220) 0.095 g

Placebo Gel Formulation #2

Carbomer 934 (lot# 00-218) 0.105 g

Propylene glycol (lot# 98-048) 8.81 g

Sodium hydroxide (0.5% in propylene glycol) 0.15 g

Alcohol (200 proof) 1.0 g

However, Placebo Gel Formulation #1 formed a turbid solution rather than a gel. Formulation #2 did form a gel.

Five more Formulations 33–37 were then prepared by adding carbomer to about 8.8 g of propylene glycol, the solution then being continuously stirred in a container overnight. Once the carbomer went into solution, permeation enhancer and THC were dissolved in 0.5 ml alcohol, and the THC solution then mixed well with carbomer solution and stirred for 15 minutes. The resulting gel formulations 33–37 were then analyzed by HPLC to determine the percent recovery (the amount of THC remaining in the gel formulation after preparation thereof). The results of these HPLC tests are shown below in Table IV.

TABLE IV

| Test product | Amount of carbomer: | Name and amount of permeation enhancer added: | Amount of THC added: | Percent recovery: | Physical appearance of gel: |
|---|---|---|---|---|---|
| Formulation-33 | 0.103 gm | — | 0.075 gm | 77.39 | Transparent |
| Formulation-34 | 0.1043 gm | Lauric acid, 0.101 gm | 0.0695 gm | 84.39 | Transparent |
| Formulation-35 | 0.100 gm | Oleic acid, 0.0958 gm | 0.089 gm | 93.15 | Transparent |
| Formulation-36 | 0.1043 gm | Caproic acid, 0.0911 gm | 0.075 gm | 88.83 | Transparent |
| Formulation-37 | 0.106 gm | Caprylic acid, 0.0966 gm | 0.092 gm | 94.98 | Transparent |

Five more gel formulations 38–42 were prepared according to the above method, and in addition, adding polymethacrylic acid to the solution. All the formulations were desirably transparent. Gel formulations 38–42 were then subjected to HPLC analysis to determine percent recovery, the results of these tests being shown in Table V below:

TABLE V

| Test product | Amount of polymethacrylic acid: | Name and amount of permeation enhancer: | Amount of THC: | Percent recovery: | Physical appearance of gel: |
|---|---|---|---|---|---|
| Formulation-38 | 1.02 gm | — | 0.055 gm | 101.06 | Transparent |
| Formulation-39 | 1.0 gm | Oleic acid 0.299 gm | 0.054 gm | 95.65 | Transparent |
| Formulation-40 | 1.001 gm | Caproic acid 0.3 gm | 0.056 gm | 94.87 | Transparent |
| Formulation-41 | 1.002 gm | Caprylic acid 0.297 gm | 0.060 gm | 82.82 | Transparent |
| Formulation-42 | 1.0 gm | Lauric acid 0.301 gm (1% solution) | 0.066 gm | 96.92 | Transparent |

Formulation of Film of THC:

About 1.0 g of PMA (100,000) was dispersed in 7.5 ml of alcohol and 2.5 ml of water, the resulting mixture then being continuously stirred for about 2 hours. Once the PMA went into solution, about 1.0 g of PEG 8000 was dissolved in 2 ml of alcohol, and this PEG solution was added to the PMA solution and continuously stirred overnight. After overnight stirring, a clear, viscous solution was obtained.

Five PMA-PEG complex solutions were prepared according to the method above, and 5% w/w permeation enhancer was added to the solution. THC was then dissolved in 1 ml of alcohol, the resulting THC solution was added to the PMA-PEG complex solution, and the mixture was continuously stirred for 20 minutes to form Formulations 23–27. Each of Formulations 23–27 were then individually spread on a petri dish covered with para-film and dried in a drying oven at a temperature below 35° C. to form a film formulation. The prepared films were translucent, and the thickness thereof varied from 0.25 mm to 0.45 mm. A fixed area of film for each Formulation 23–27 was then cut and subjected to HPLC analysis, the results of the HPLC analysis being shown in Table VI below:

TABLE VI

| Test product | Permeation enhancer (5% w/w) | Amount of PMA Added: | Amount of PEG Added: | Amount THC Added: | Percent recovery: |
|---|---|---|---|---|---|
| Formulation-23 | Caprylic acid | 1.021 gm | 1.024 gm | 67.4 gm | 70.96 |
| Formulation-24 | Caproic acid | 1.00 gm | 1.01 gm | 81.7 mg | 59.49 |
| Formulation-25 | Oleic acid | 1.012 gm | 1.014 gm | 66.0 mg | 62.52 |
| Formulation-26 | Lauric acid | 1.017 gm | 1.012 gm | 62.4 mg | 69.09 |
| Formulation-27 | — | 1.013 gm | 1.027 gm | 63.3 Mg | 72.38 |

Each of the film formulations 23 to 27 shown above were used for in vitro skin permeation studies.

In Vitro Skin Permeation Studies:

Permeation experiments were assessed using a Franz diffusion assembly. Both rat and human skin were used for the study. Initially, full thickness normal rat skin was used. Hairs were removed from the skin using a clipper. Before mounting into the diffusion cell, the subcutaneous fat layer was separated from the skin. It was cut according to the size of the donor cell, with a surface area of 0.64 cm$^2$. The skin was mounted in between the donor and receiver compartment. The receiver compartment contained a 50% hydro-alcoholic (water:ethanol) solution for ensuring the pseudo-sink conditions by increasing the solubility of THC in the medium. Temperature was maintained at 37° C. Two formulations, Formulations 3 and 4, were tested to determine the permeation ability of the formulations into skin.

Figure 2:
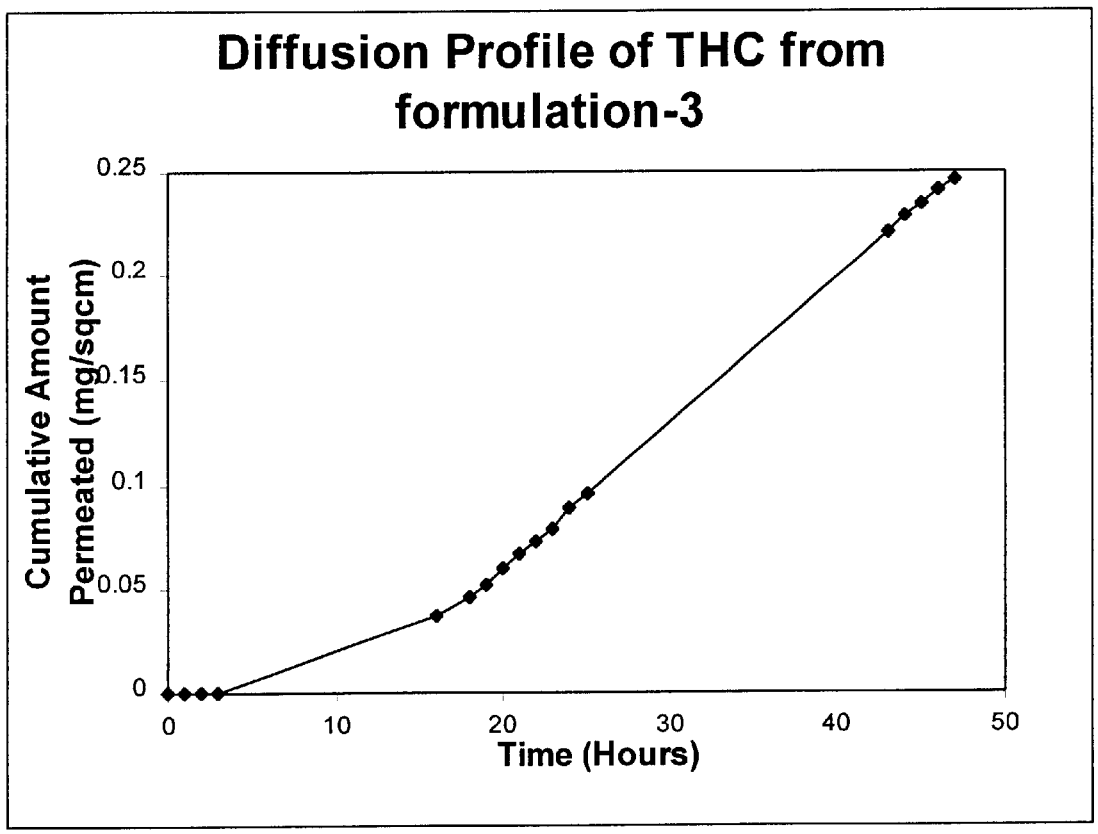
FIG. 2 is a graph illustrating the diffusion profile (cumulative amount of THC permeated into a section of skin vs. time) for Formulation 3 of the present invention.
Figure 3:
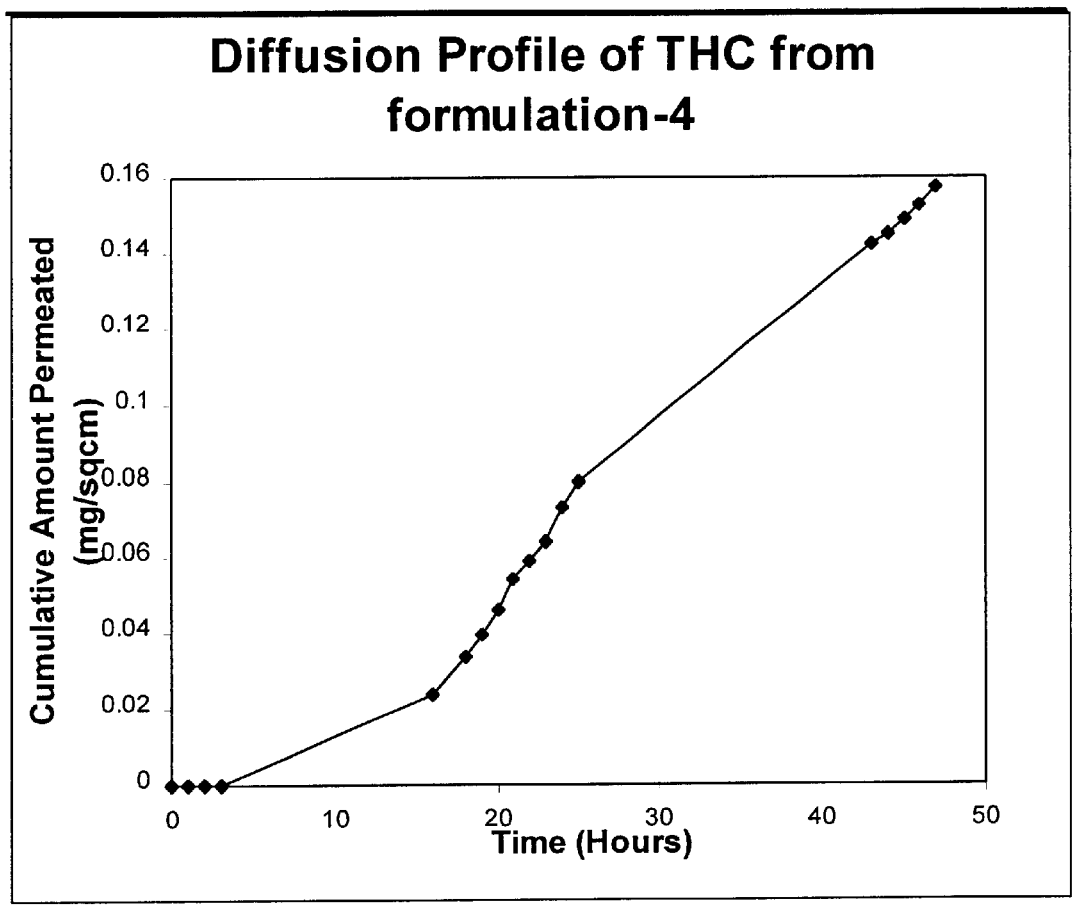
FIG. 3 is a graph illustrating the diffusion profile (cumulative amount of THC permeated into a section of skin vs. time) for Formulation 4 of the present invention.

Formulation 3 contained 8.6 mg/ml of THC, and Formulation 4 contained 9.86 mg/ml of THC. The donor compartment contained 0.5ml of the formulation, and the receiver compartment contained 5.1 ml of the hydro-alcoholic solutions. Two hundred microliters (200 µl) of sample was withdrawn and replaced with fresh amount of fluid. Samples were withdrawn from the tested skin at 0, 1, 2, 3, 16, 17, 18, 19, 20, 21, 22, 23, 24, 25, 26, 42, 43, 44, 45, 46, 47, and 48 hours. The results of the permeations tests are shown graphically herein in FIGS. 2 and 3.

Samples were then analyzed by HPLC. The results of the HPLC analysis for Formulation 3 is shown in Table VII below, and the results of the HPLC analysis of Formulation 4 is shown in Table VIII below:

TABLE VII

| Time (Hours) | Peak Area | Conc. (ug/mL) | Amt. perm. (mg) | Cumu/sqcm 0 | Flux 0 | % Amt. perm. |
|---|---|---|---|---|---|---|
| 0 | 0 | 0.00 | 0 | 0 | 0 | 0 |
| 1 | 0 | 0.00 | 0 | 0 | 0 | 0 |
| 2 | 0 | 0.00 | 0 | 0 | 0 | 0 |
| 3 | 0 | 0.00 | 0 | 0 | 0 | 0 |
| 16 | 268534 | 7.26 | 0.037 | 0.05785062 | 0.00445 | 0.861032542 |

TABLE VII-continued

| Time (Hours) | Peak Area | Conc. (ug/mL) | Amt. perm. (mg) | Cumu/sqcm 0 | Flux 0 | % Amt. perm. |
|---|---|---|---|---|---|---|
| 18 | 323474 | 8.77 | 0.046 | 0.07213067 | 0.00714 | 1.073572689 |
| 19 | 349958 | 9.49 | 0.052 | 0.08066048 | 0.00853 | 1.200528071 |
| 20 | 395377 | 10.74 | 0.060 | 0.09355707 | 0.012897 | 1.392477294 |
| 21 | 427690 | 11.63 | 0.067 | 0.10397773 | 0.010421 | 1.547575536 |
| 22 | 458520 | 12.47 | 0.073 | 0.11435121 | 0.010373 | 1.70197149 |
| 23 | 480791 | 13.08 | 0.079 | 0.12311778 | 0.008767 | 1.832450688 |
| 24 | 534427 | 14.55 | 0.089 | 0.13893254 | 0.015815 | 2.067833201 |
| 25 | 564912 | 15.39 | 0.096 | 0.15014572 | 0.011213 | 2.234726962 |
| 43 | 1432401 | 39.19 | 0.221 | 0.34461227 | 0.010804 | 5.129112784 |
| 44 | 1431227 | 39.16 | 0.228 | 0.35660281 | 0.011991 | 5.307576646 |
| 45 | 1414268 | 38.69 | 0.234 | 0.36513225 | 0.008529 | 5.434526478 |
| 46 | 1410365 | 38.59 | 0.241 | 0.37637069 | 0.011238 | 5.601796298 |
| 47 | 1391135 | 38.06 | 0.246 | 0.38422476 | 0.007854 | 5.718694174 |
| 48 | 1413615 | 38.68 | 0.254 | 0.39611817 | 0.011893 | 5.895712372 |

TABLE VIII

| Time (Hours) | Peak Area | Conc. (ug/ml) | Amt. perm. (mg) | Cumu/sqcm 0 | Flux 0 | % Amt. perm. |
|---|---|---|---|---|---|---|
| 0 | 0 | 0.00 | 0 | 0 | 0 | 0 |
| 1 | 0 | 0.00 | 0 | 0 | 0 | 0 |
| 2 | 0 | 0.00 | 0 | 0 | 0 | 0 |
| 3 | 0 | 0.00 | 0 | 0 | 0 | 0 |
| 16 | 173295 | 4.65 | 0.024 | 0.03702877 | 0.0028484 | 0.480698018 |
| 18 | 237486 | 6.41 | 0.034 | 0.05251479 | 0.007743 | 0.68173357 |
| 19 | 269662 | 7.29 | 0.039 | 0.0615518 | 0.009037 | 0.799049766 |
| 20 | 305780 | 8.28 | 0.046 | 0.07172651 | 0.0101747 | 0.931135215 |
| 21 | 352797 | 9.57 | 0.054 | 0.0845937 | 0.0128672 | 1.09817378 |
| 22 | 375114 | 10.18 | 0.059 | 0.0924639 | 0.0078702 | 1.200342689 |
| 23 | 396636 | 10.77 | 0.064 | 0.10035163 | 0.0078877 | 1.302739152 |
| 24 | 445259 | 12.11 | 0.073 | 0.1143489 | 0.0139973 | 1.484448136 |
| 25 | 474235 | 12.90 | 0.080 | 0.12446767 | 0.0101188 | 1.61580746 |
| 43 | 901926 | 24.64 | 0.142 | 0.22200489 | 0.0054187 | 2.882010786 |
| 44 | 884752 | 24.17 | 0.145 | 0.2259493 | 0.0039444 | 2.933216102 |
| 45 | 880096 | 24.04 | 0.149 | 0.23248325 | 0.0065339 | 3.018038091 |
| 46 | 871258 | 23.80 | 0.152 | 0.23806297 | 0.0055797 | 3.090472659 |
| 47 | 871824 | 23.81 | 0.157 | 0.2456229 | 0.0075599 | 3.188613655 |
| 48 | 867988 | 23.71 | 0.162 | 0.25306393 | 0.007441 | 3.285211246 |

Further, in vitro skin permeation studies were conducted using Formulation #43, a transdermal gel, which was prepared as follows:

Pemulen was first dissolved in a mixture of ethanol and water, triethanolamine was added thereto, and the resultant mixture was mixed well to firm a first pemulen solution. Tetrahydrocannabinol (THC) was then dissolved in a portion of alcohol, and isopropylmyristate was then added thereto, to form a second THC solution. Both the first pemulen solution and the second THC solution were mixed for 30 minutes, and a transparent gel was subsequently formed.

This gel had a pH of 6.0. There were no gritty particles. An irritation study was conducted for the formulation on a rat, the results of this study indicating that the formulation did not induce any redness associated with erythema when applied transdermlly. The Formulation #43 had the following formula:

Tetrahydrocannbinol($\Delta 9$ THC) 1.0%
Triethanolamine 0.5%
Isopropylmyristate 1.0%
Pemulen (polymers of acrylic acid) 1.0%
Ethanol-200 proof 70.0%
Purified water 26.5.0%

Permeation experiments on rat skin were performed for Formulation 43, as described above for Formulations 3 and 4. The results of these permeation experiments are shown below in Table IX.

TABLE IX

| Time (Hours) | Peak Area | Conc. (ug/mL) | Amt. perm. (mg) | Cumu. mg/sqcm | Flux mg/sq.cm.hr | % Amt. perm |
|---|---|---|---|---|---|---|
| 0 | 0 | | | 0 | | |
| 2 | 98.3 | 2.599688069 | 0.01351838 | 0.02112247 | 0.010561233 | 0.26769 |
| 17 | 942.5 | 24.54406031 | 0.12814905 | 0.20023289 | 0.011940695 | 2.5376 |
| 20 | 1057.24 | 27.52664414 | 0.1485673 | 0.2321364 | 0.010634504 | 2.94193 |
| 26 | 1460.97 | 38.02131531 | 0.20864492 | 0.32600768 | 0.015645213 | 4.13158 |
| 41 | 2002.67 | 52.10241747 | 0.28947091 | 0.4522983 | 0.008419374 | 5.7321 |
| 44 | 2064.32 | 53.70496491 | 0.30822464 | 0.481601 | 0.009767568 | 6.10346 |
| 47 | 2235.19 | 58.14660775 | 0.34206218 | 0.53447215 | 0.017623717 | 6.77351 |

Figure 4:
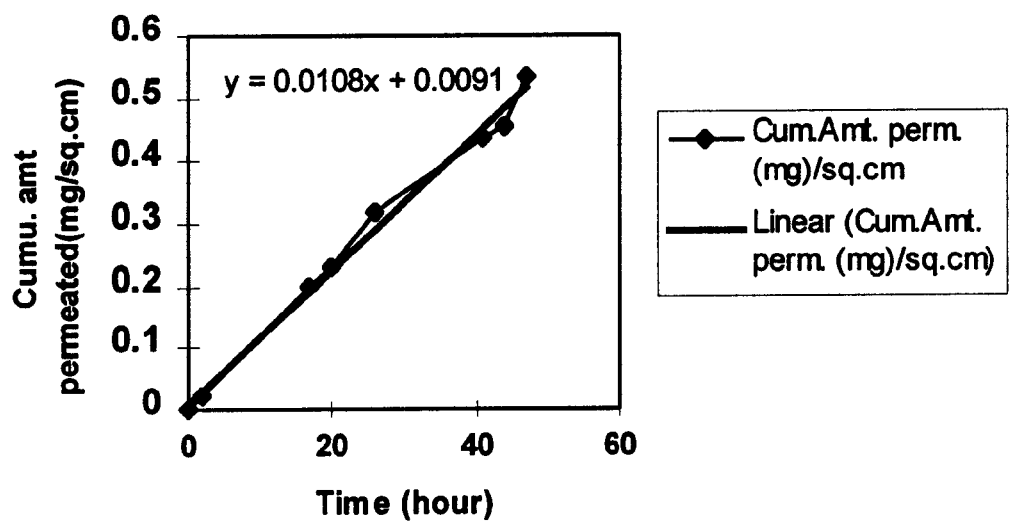
FIG. 4 is a graph illustrating the diffusion profiled (cumulative amount of THC permeated into a section of skin vs. time) for Formulation 43 of the present invention.

The data presented above in Table IX was then graphed to illustrate the permeation of THC into the skin over time. This graph is shown in FIG. 4 herein.

Thus, after extensive experimentation, the present inventors discovered that transdermal THC administration overcomes the problem of variation in absorption and metabolism associated with oral administration. Further, it was unexpectedly discovered that transdermal administration increases bioavailability and the efficacy of THC by avoiding the liver first-pass inactivation, which significantly lowers the plasma, and brain concentration, of THC administered orally. Therefore, small doses of THC can be administered to a patient, resulting in fewer side effects, and the drug is more tolerable and more effective in treating patients.

Additionally, as THC is heavily metabolized by the liver, transdermal/transcutaneous administration of THC, as opposed to oral administration, may help to reduce drug-drug interactions with the other drugs that are also extensively metabolized by the liver. The in vitro skin permeation data shown in FIGS. 2–4 suggests that zero order kinetics were followed from all formulations, and that 10.8 g/sq.cm./hr transdermal gel delivery is feasible to achieve the desired systemic effect. A steady state flux of 8.8 g/sq.cm./hr was estimated based on the total clearance and minimum effective concentration.

The pharmaceutical composition of the present invention is useful, but not limited to, treating pain, nausea, vomiting (particularly that associated with chemotherapy in cancer patients), glaucoma, arthritis, dementia, multiple sclerosis, and for deterring weight loss in AIDS patients.

What is claimed is:

1. A pharmaceutical composition comprising tetrahydrocannabinol (THC), ethanol, polyethylene glycol, polymethacrylic acid, isopropyl myristate, carbopol, triethanolamine, propylene glycol, and acetone.

2. The pharmaceutical composition of claim 1, further comprising:
   from greater than 0 to 5 wt % tetrahydrocannabinol (THC);
   40–70 wt % ethanol;
   3–10 wt % polyethylene glycol;
   5–20 wt % polymethacrylic acid;
   from greater than 0 to 5 wt % isopropyl myristate;
   from greater than 0 to 10 wt % carbopol;
   from greater than 0 to 5 wt % triethanolamine;
   5–50 wt % propylene glycol; and
   20–50 wt % acetone.

3. The pharmaceutical composition of claim 1, comprising:
   about 0.5 to about 2 wt % tetrahydrocannabinol (THC);
   about 65 wt % ethanol;
   about 4.7 to about 5.7 wt % polyethylene glycol;
   about 10 to about 14 wt % polymethacrylic acid;
   about 0.5 to about 1 wt % isopropyl myristate;
   from greater than 0 to about 5 wt % carbopol;
   from about 0.47 to about 1 wt % triethanolamine;
   from about 10 to about 30 wt % propylene glycol;
   about 35 wt % acetone, and
   water.

4. The pharmaceutical composition of claim 1, further containing a permeation enhancer.

5. The pharmaceutical composition of claim 4, wherein the pharmaceutical composition contains 2–10 wt % permeation enhancer.

6. The pharmaceutical composition of claim 4, wherein the pharmaceutical composition contains about 5 wt % permeation enhancer.

7. The pharmaceutical composition of claim 4, wherein the permeation enhancer is caproic acid.

8. The pharmaceutical composition of claim 4, wherein the permeation enhancer is caprylic acid.

9. The pharmaceutical composition of claim 4, wherein the permeation enhancer is lauric acid.

10. The pharmaceutical composition of claim 4, wherein the permeation enhancer is oleic acid.

11. The pharmaceutical composition of claim 4, wherein the permeation enhancer is TWEEN 80.

12. The pharmaceutical composition of claim 4, wherein the permeation enhancer is selected from the group consisting of caproic acid, caprylic acid, lauric acid, oleic acid and TWEEN 80.

13. A method of manufacturing the composition of claim 1 comprising:
   (a) combining/mixing ethanol, polyethylene glycol, polymethacrylic acid, tetrahydrocannabinol (THC), isopropyl myristate, carbopol, triethanolamine, optionally a permeation enhancer, propylene glycol, acetone, and water to form a complex;
   (b) drying the complex using heat to form a dried complex;
   (c) milling the dried complex to form a powder; and
   (d) adding a lower alcohol to the powder to form a gel.

14. The method of manufacturing of claim 13, further comprising mixing the elements in step (a) at a temperature of from 25–70° C.

15. The method of manufacturing of claim 13, further comprising drying the complex of step (b) at a temperature of from 25–70° C.

16. The method of manufacturing the composition of claim 13, further comprising performing the drying step (b) for 4–12 hours.

17. The method of manufacturing the composition of claim 14 further comprising mixing the components in step (a) for 1–4 hours.

18. The method of manufacturing of claim 13, further comprising mixing the components in step (a) at a stirring rate of 60–300 RPM's.

19. The method of manufacturing of the composition of claim 1, comprising:
   (a) combining/mixing ethanol, polyethylene glycol, polymethacrylic acid, tetrahydrocannabinol (THC), isopropyl myristate, carbopol, triethanolamine, a permeation enhancer, propylene glycol, acetone, and water at a temperature of from 25–70° C., and stirring same at a rate of 60–300 RPM's for 1–4 hours to form a complex;
   (b) drying the complex at a temperature of from 25–70° C. for 1–4 hours to form a dried complex;
   (c) milling the dried complex to form a powder; and
   (d) adding a lower alcohol to the powder to form a gel.

20. A method of manufacturing the composition of claim 1 comprising:
   (a) combining/mixing ethanol, polyethylene glycol, polymethacrylic acid, tetrahydrocannabinol (THC), isopropyl myristate, carbopol, triethanolamine, a permeation enhancer, propylene glycol, acetone, and water at a temperature of from 40–60° C., and stirring same at a rate of 60–300 RPM's for 1–4 hours to form a complex;
   (b) drying the complex at a temperature of 40–60° C. for 1–4 hours to form a dried complex;
   (c) milling the dried complex to form a powder; and
   (d) adding a lower alcohol to the powder to form a gel.

21. A method of manufacturing the pharmaceutical composition of claim 1, comprising:

mixing carbopol and polymethacrylic acid in ethanol to form a first solution; mixing polyethylene glycol or polypropylene glycol in ethanol to form a second solution;

mixing the first and second solutions to form a third solution;

mixing isopropyl myristate and triethanolamine into the third solution as necessary;

mixing tetrahydrocannabinol with ethanol to form a fourth solution;

mixing the third and fourth solutions to form a pharmaceutical composition according to the present invention.

22. A transdermal/transcutaneous delivery system for THC comprising the pharmaceutical composition of claim 1.

23. The transdermal/transcutaneous delivery system of claim 22, further comprising a gel, patch or cloth for application onto the skin of a patient.

24. A method for manufacturing the gel, patch or cloth of claim 23 comprising adding the pharmaceutical composition of claim 2 to a gel, patch or cloth suitable for application against human or animal skin.

25. A method of manufacturing a transdermal patch or cloth containing a pharmaceutical composition containing THC comprising:

adding carbopol/poly methacrylic acid in ethanol to polyethylene glycol or propyleneglycol in ethanol to form a first solution, mixing the first solution with a solution containing isopropyl myristate or triethanolamine to form a second solution, mixing the second solution with a mixture of tetrahydrocannabinol and ethanol to obtain a viscous solution or gel, and applying the gel or viscous solution to a transdermal patch or cloth for direct application to human or animal skin.

26. A method of manufacturing gel containing a pharmaceutical composition containing tetrahydrocannibinol ($\Delta 9$ THC) comprising:

a first step comprising mixing carbopol and trolamine in an ethanol:water mixture to form a first viscous solution, a second step comprising mixing the first viscous solution with a second solution containing ethanol and isopropyl myristate to obtain a third solution, and a third step comprising mixing the third solution with a fourth solution containing $\Delta 9$ THC and ethanol to obtain a gel for the direct application to human and/or animal skin.

27. A method for manufacturing a pharmaceutical composition comprising a transdermal gel containing extracts of cannabis, said method comprising:

a first supercritical fluid extraction step wherein 9 THC is extracted from cannabis, a second step comprising dispersing the 9 THC in an ethanol:water mixture, a third step comprising adding trolamine to the ethanol:water mixture to form a first solution, and a fourth step comprising mixing the first solution with a second solution containing ethanol and isopropyl myristate to form a third solution, wherein the third solution is a translucent gel for direct application to human skin.

* * * * *